US011052085B2

United States Patent
Balasubramaniam et al.

(10) Patent No.: US 11,052,085 B2
(45) Date of Patent: Jul. 6, 2021

(54) METHODS FOR TREATING SKELETAL MUSCLE CACHEXIA ARISING FROM BURN INJURY BY ADMINISTERING PDE4B-SELECTIVE INHIBITORS

(71) Applicants: University of Cincinnati, Cincinnati, OH (US); Shriners Hospital for Children, Tampa, FL (US)

(72) Inventors: Ambikaipakan Balasubramaniam, Mason, OH (US); Sulaiman Sheriff, West Chester, OH (US)

(73) Assignees: University of Cincinnati, Cincinnati, OH (US); Shriners Hospital For Children, Tampa, FL (US)

( * ) Notice: Subject to any disclaimer, the term of this patent is extended or adjusted under 35 U.S.C. 154(b) by 129 days.

(21) Appl. No.: 16/202,878

(22) Filed: Nov. 28, 2018

(65) Prior Publication Data

US 2019/0160064 A1 May 30, 2019

Related U.S. Application Data

(60) Provisional application No. 62/591,249, filed on Nov. 28, 2017.

(51) Int. Cl.
*A61K 31/506* (2006.01)
*A61P 21/00* (2006.01)
*A61K 31/522* (2006.01)
*A61K 31/4985* (2006.01)
*A61K 31/53* (2006.01)
*A61K 31/519* (2006.01)

(52) U.S. Cl.
CPC ........ *A61K 31/506* (2013.01); *A61K 31/4985* (2013.01); *A61K 31/519* (2013.01); *A61K 31/522* (2013.01); *A61K 31/53* (2013.01); *A61P 21/00* (2018.01)

(58) Field of Classification Search
None
See application file for complete search history.

(56) References Cited

U.S. PATENT DOCUMENTS

2006/0079540 A1* 4/2006 Schmidt .................. A61P 31/18
514/263.34
2006/0293343 A1* 12/2006 Naganuma ........... C07D 417/04
514/256

OTHER PUBLICATIONS

Hosokawa et al., Am J Physiol Endocrinol Metab 304: E922-E933, 2013 (Year: 2013).*
Richard T. Hinkle et al, "Phosphodiesterase 4 Inhibition Reduces Skeletal Muscle Atrophy"; Muscle Nerve 32: 775-781, 2005.
Sachikol-Hosokawa et al, "Title efficacy of phosphodiesterase 5 inhibitor on distant burn-induced muscle autophagy, microcirculation, and survival rate"; Am J Physiol Endocrinol Metab 304: E922-E933, 2013.
Rashika Joshi et al, "Phosphodiesterase (PDE) inhibitor torbafylline (HWA 448) attenuates burn-induced rat skeletal muscle proteolysis through the PDE4/cAMP/EPAC/P13K/Akt pathway"; Molecular and Cellular Endocrinology 393 (2014) 152-163.

* cited by examiner

*Primary Examiner* — Karl J Puttlitz
(74) *Attorney, Agent, or Firm* — Dinsmore & Shohl LLP

(57) ABSTRACT

A method of treating skeletal muscle cachexia and inflammation associated with burn injury in a subject in need thereof is provided, the method including administering to the subject an effective amount of a phosphodiesterase-4B (PED4B)-selective inhibitor.

7 Claims, 5 Drawing Sheets
Specification includes a Sequence Listing.

A

B

METHODS FOR TREATING SKELETAL MUSCLE CACHEXIA ARISING FROM BURN INJURY BY ADMINISTERING PDE4B-SELECTIVE INHIBITORS

CROSS REFERENCE TO RELATED APPLICATIONS

This application claims priority to U.S. Provisional Application Ser. No. 62/591,249, filed Nov. 28, 2017, which application is hereby incorporated by reference in its entirety.

TECHNICAL FIELD

This disclosure relates to the field of burn injury therapy. More specifically, this disclosure relates to methods of treating skeletal muscle cachexia due to burn injury by administering PDE4B-selective inhibitors.

BACKGROUND

Burn injuries result in activation of a pro-inflammatory cascade, which contributes to most, if not all, burn-induced dysfunctions. This activation has been attributed to a profound and prolonged production of proinflammatory mediators. In addition, burn injury also results in increased production of catabolic hormones and a reduction in anabolic hormones. These events result in hypermetabolism, which persists even after wound healing, leading to increased lipolysis, depletion of hepatic glycogen stores, and ultimately to the breakdown of skeletal muscle. Muscle loss results in decreased strength, making rehabilitation difficult. Consequently, severely burned children experience stunted growth, minimal weight gain and no apparent increase in lean body mass (LBM) for long time periods. Despite advancement in burn care and improved survival, no satisfactory drugs are available, to date, to treat loss of LBM in burn injury.

In this regard, it is known in the art that inhibitors of PDE4, a major regulator of intracellular cAMP concentrations, can attenuate muscle atrophy in animal models with denervation, casting, sepsis, or cancer. The PDE4 family is the most predominant PDE in human and rodent skeletal muscles and accounts for more than 80% of PDE activity. PDE4 isoforms include PDE4A, PDE4B, PDE4C, and PDE4D.

However, not much effort has been taken to date to develop PDE4-based drugs to treat muscle cachexia, due to the fact that PDE4 inhibitors cause adverse effects, including nausea and emesis, which has been associated with inhibition of PDE4D.

A need exists for improved, targeted therapies for treating patients suffering from skeletal muscle cachexia and inflammation arising from burn injury.

SUMMARY

Consistent with these findings, the present inventors have now investigated the PDE4 isoforms involved in skeletal muscle cachexia using wild type (WT) and PDE4B knockout (KO) rat models. These studies reveal that PDE4B, which is highly expressed in the human skeletal muscle, plays a predominant role in muscle cachexia in burn injury.

Accordingly, provided herein is a method of treating skeletal muscle cachexia associated with burn injury in a subject in need thereof, the method comprising administering to the subject an effective amount of a phosphodiesterase-4B (PDE4B)-selective inhibitor.

These and other objects, features, embodiments, and advantages will become apparent to those of ordinary skill in the art from a reading of the following detailed description and the appended claims.

DETAILED DESCRIPTION

Figure 1:
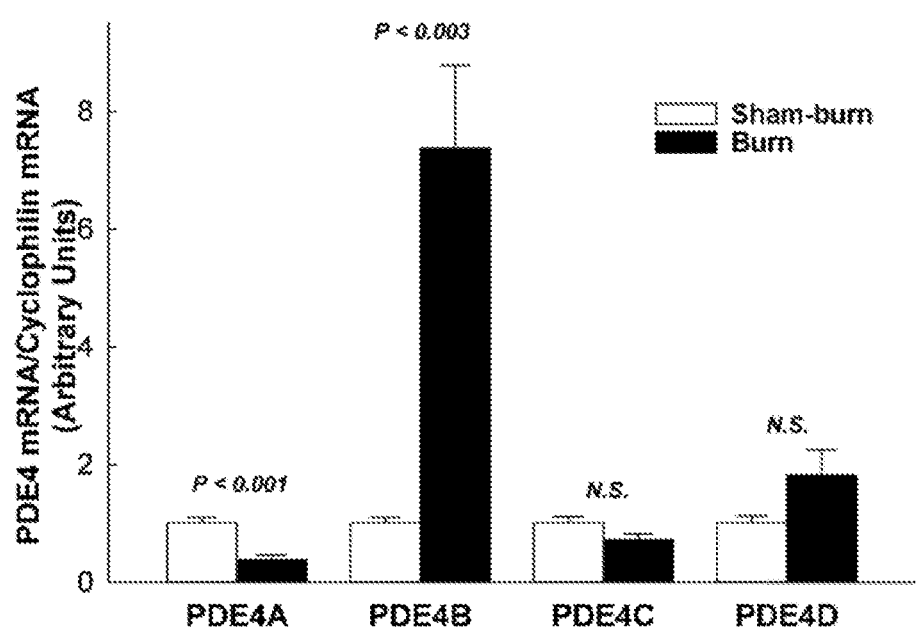
FIG. 1. Expression of PDE4 isoforms in EDL muscles of WT rats 1 day after burn injury. Burn injury increased mRNA expression of PDE4B (p<0.003 vs. sham controls) and decreased mRNA expression of PDE4A (p<0.003 vs. sham controls) in WT-rat EDL on day 1 after burn, (n=7-8 per group).

The details of one or more embodiments of the presently-disclosed subject matter are set forth in this document. Modifications to embodiments described in this document, and other embodiments, will be evident to those of ordinary skill in the art after a study of the information provided herein.

While the following terms are believed to be well understood by one of ordinary skill in the art, definitions are set forth to facilitate explanation of the presently-disclosed subject matter. Unless defined otherwise, all technical and scientific terms used herein have the same meaning as commonly understood by one of ordinary skill in the art to which the presently-disclosed subject matter belongs.

Unless otherwise indicated, all numbers expressing quantities of ingredients, properties such as reaction conditions, and so forth used in the specification and claims are to be understood as being modified in all instances by the term "about." Accordingly, unless indicated to the contrary, the numerical parameters set forth in this specification and claims are approximations that can vary depending upon the desired properties sought to be obtained by the presently-disclosed subject matter.

As used herein, the term "about," when referring to a value or to an amount of mass, weight, time, volume, pH, size, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

An "effective amount," as used herein, refers to an amount of a substance (e.g., a therapeutic compound and/or composition) that elicits a desired biological response. In some embodiments, an effective amount of a substance is an amount that is sufficient, when administered to a subject suffering from or susceptible to a disease, disorder, and/or condition, to treat, diagnose, prevent, and/or delay and/or alleviate one or more symptoms of the disease, disorder, and/or condition. As will be appreciated by those of ordinary skill in this art, the effective amount of a substance may vary depending on such factors as the desired biological endpoint, the substance to be delivered, the target cell or tissue, etc. For example, the effective amount of a formulation to treat a disease, disorder, and/or condition is the amount that alleviates, ameliorates, relieves, inhibits, prevents, delays onset of; reduces severity of and/or reduces incidence of one or more symptoms or features of the disease, disorder, and/or condition. Furthermore, an effective amount may be administered via a single dose or via multiple doses within a treatment regimen. In some embodiments, individual doses or compositions are considered to contain an effective amount when they contain an amount effective as a dose in the context of a treatment regimen. Those of ordinary skill in the art will appreciate that a dose or amount may be considered to be effective if it is or has been demonstrated to show statistically significant effectiveness when administered to a population of patients; a particular result need not be achieved in a particular individual patient in order for an amount to be considered to be effective as described herein.

The terms "treat," "treatment," and "treating," as used herein, refer to a method of alleviating or abrogating a disease, disorder, and/or symptoms thereof in a subject.

As used herein, "skeletal muscle cachexia" refers to the proteolysis, or protein breakdown, of skeletal muscle. In embodiments, skeletal muscle cachexia is associated with burn injury, i.e., skeletal muscle cachexia results from hyperinflammation and hypercatabolism that persists chronically post-burn injury. In embodiments, skeletal muscle cachexia is characterized by systemic loss of muscle mass and lean body mass of a subject.

As used herein, a "PDE4B-selective inhibitor" refers to a compound or a pharmaceutical salt thereof that inhibits PDE4B enzyme, while substantially avoiding inhibition of other PDE families (i.e., PDE1-3 and PDE5-11) or other PDE4 subtypes (i.e., PDE4A, PDE4C, PDE4D).

As used herein, a "subject" refers to a mammal. Optionally, a subject is a human or non-human primate. Optionally, the subject is selected from the group consisting of mouse, rat, rabbit, monkey, pig, and human. In a specific embodiment, the subject is a human.

As used herein, the term "sequentially" refers to a treatment protocol in which administration of a first therapeutic agent is followed by administration of a second therapeutic agent.

As used herein, the term "contemporaneously" refers to administration of a first therapeutic agent and administration of a second therapeutic agent, wherein the first and second therapeutic agents are separate and are administered at substantially the same time.

Phosphodiesterases (PDEs) are a class of enzymes involved in phosphoric diester hydrolytic cleavage, particularly phosphodiesterases that cleave cyclic nucleotides important for cell signaling. In mammals, PDEs are grouped into 11 families, PDE1-PDE11.

The PDE4 family encompasses four genes encoding the isoform subtypes PDE4A, PDE4B, PDE4C, and PDE4D. PDE4B comprises three domains: an N-terminal regulatory domain, a catalytic domain, and a C-terminal domain.

It has been known for sometime that inhibitors of PDE4, a major regulator of intracellular cAMP concentrations, can attenuate muscle atrophy in animal models with denervation, limb immobilization, sepsis, or cancer. Moreover, the PDE4 family is the predominant PDE in human and rodent skeletal muscles, and accounts for more than 80% of PDE activity. Consistent with these findings, it has been demonstrated that burn injury causes rat skeletal muscle PDE4 activity to increase by 3-fold, with PDE4 activity constituting>75% of total muscle PDE activity. Moreover, torbafylline, a non-selective PDE inhibitor, significantly attenuated burn-induced skeletal muscle proteolysis through normalizing PDE4 activity and cAMP concentrations, and activating the EPAC/PI3K/Akt pathway. Joshi, et al., *Phosphodiesterase (PDE) inhibitor torbafylline (HWA 448) attenuates burn-induced rat skeletal muscle proteolysis through the PDE4/cAMP/EPAC/PI3K pathway*, Mol. & Cell. Endocrin. 393: 152-63 (2014), incorporated herein by reference in its entirety. Based on these findings, and in view of the therapeutic potential of PDE4 inhibitors, the inventors have investigated the PDE4 isoforms involved in skeletal muscle proteolysis using wild type (WT) and PDE4B knockout (KO) rat models. These studies indicate that PDE4B, which is highly expressed in human skeletal muscle, plays a predominant role in muscle cachexia associated with burn injury.

The presently disclosed studies to determine the PDE4 isoform(s) involved in mediating skeletal muscle proteolysis revealed that burn injury increased the expression of rat skeletal muscle PDE4B mRNA by 6-fold, but had little or no effect on expression of other PDE4 isoforms. The effects of burn injury on PDE4B-KO rats is described herein. Burn injury significantly increased EDL muscle total and myofibrillar proteolysis in WT rats, but PDE4B-KO markedly reduced EDL muscle total (41%→11%) and myofibrillar (167%→28%) proteolysis compared to that in WT rats. Moreover, burn injury increased PDE4 activity in the skeletal muscle of WT rats, but this was reduced by ~85% in PDE4B KO rats. Further, burn injury decreased skeletal muscle weight and cAMP concentration in WT rats, but had no significant effects in the muscles of PDE4B KO rats. Incubation of the EDL muscle of burn-PDE4B KO with EPAC inhibitor, but not with PKA inhibitor, eliminated the protective effects of PDE4B KO on EDL muscle proteolysis, and increased muscle proteolysis to the same extent as in the EDL of burn-WT rats. These novel findings confirm a major role for PDE4B in skeletal muscle proteolysis in burn injury and suggest that therapy based on PDE4B-selective inhibitors is useful for the treatment of skeletal muscle cachexia in burn injury, without the fear of causing nausea and emesis associated with PDE4D inhibition.

The instant studies show that: 1) burn injury primarily elevated skeletal muscle mRNA expression of PDE4B (FIG. 1); and 2) PDE4B KO imparts remarkable resistance to burn-induced skeletal muscle proteolysis (FIGS. 2A and 2B). The latter findings are consistent with previous reports that various pathophysiological conditions modulate the expression and activity of various PDE isoforms selectively and in a tissue-dependent manner. For example, only PDE4D activity and PDE4D mRNA expression were increased in lung tissue in a murine model of asthma, and these changes were normalized by the PDE4 inhibitor, ciclamilast. Deng, et al., *Effects of ciclamilast, a new PDE4 inhibitor, on airway hyperresponsiveness, PDE4D expression and airway inflammation in a murine model of asthma, Eur. J. Pharmacol.* 547: 125-35 (2006). PDE4C, and not PDE4A, PDE4B or PDE4D, was significantly upregulated in the lungs from ovalbumin-sensitized rats, suggesting PDE4C may play an important role in air way inflammation. Sheriff, et al., *Des-Acyl Ghrelin Exhibits Pro-Anabolic and Anti-Catabolic Effects on C2C12 Myotubes Exposed to Cytokines and Reduces Burn-Induced Muscle Proteolysis in Rats, Mol. Cell Endocrinol.* 351: 286-95 (2012). Only ablation of PDE4B impacted LPS-induced TNF production in mouse peritoneal macrophages.

Although burn injury modulated the expression of PDE4A mRNA by ~50%, this is much less than the 600% increase in the mRNA expression of PDE4B mRNA, and may not play any major role in muscle cachexia because ablation of PDE4B itself was sufficient to protect against burn-induced muscle proteolysis.

PDE4B KO resulted in >80% loss in burn-induced skeletal muscle PDE4 activity relative to that of WT (FIG. 3A). Moreover, burn injury increased the skeletal muscle total PDE activity in WT, but had no effects in PDE4B KO rats. Results indicate that increases in skeletal muscle total PDE and PDE4 activity following burn injury are primarily due to the elevation in PDE4B activity. These observations are also in agreement with the finding that burn injury predominantly increased the mRNA expression of EDL muscle PDE4B, but had a little or no effects on other PDE4 isoforms. Results further indicate that burn injury did not modulate the activities of other skeletal muscle PDEs or PDE4 isoforms to compensate for the absence of PDE4B in the KO rats. Results indicate that suppression of PDE4B activity is not expected to modulate the expression and activities of other PDEs.

Muscle cAMP decreased significantly following burn injury in WT rats, but remained at control levels in the burn-PDE4B-KO rats (FIG. 3B), which indicates that muscle cAMP homeostasis is predominantly regulated by PDE4B in burn injury. While not desiring to be bound by theory, it is believed that cAMP levels, which remained at normal levels in the muscles of burn-PDE4B KO rats, may play a role in imparting resistance to proteolysis in these KO rats. Consistently, incubating the muscles of burn-PDE4B KO rats with the inhibitor of EPAC, downstream element of cAMP, alleviated the resistance to proteolysis imparted by PDE4B KO, and increased the muscle protein breakdown to the same extent as in the muscles of burn-WT rats. H89, a PKA inhibitor, did not exhibit any effects, suggesting that cAMP-PKA pathway may not play role in burn-induced muscle proteolysis. Results indicate that PDE4B KO protects against muscle proteolysis via cAMP-EPAC pathway, which may in turn activate PI3K/Akt signaling cascade and counteract the deleterious downstream signals, FOXO and E3 ligases, triggered by burn injury.

The present disclosure that PDE4B KO prevents burn-induced modulation in muscle PDE and PDE4 activities, cAMP concentrations and proteolysis suggest that the PDE4B→cAMP pathway plays a crucial role in muscle atrophy associated with burn injury. Moreover, it has been shown that intracellular cAMP can modulate the expression and activities of PDE4 isoforms through inducible cAMP early repressor (ICER), a transcription factor, in a PKA dependent manner. While not desiring to be bound by theory, the data indicate that intracellular cAMP and PDE4B operate in a closed feedback loop in skeletal muscle maintaining each other's level and activity and any stimuli that disrupt this closed loop can lead to the loss of skeletal muscle integrity. With regard to burn injury, inflammatory cytokines may be responsible for the disruption of this balance through the induction of PDE4B expression because TNFα and other cytokines have been found to induce the expression of PDE4B in glial cells. This proposition is also further supported by previous findings that: 1) burn injury can increase the expression of inflammatory cytokines in skeletal muscles; and 2) TNFα+IFNγ treatment of mouse myotubes, C2C12, selectively induced PDE4B mRNA expression and increased protein breakdown, and that torbafylline treatment normalized PDE4B expression as well as proteolysis.

Recently, Tadalafil, a PDE5 inhibitor, has been shown to attenuate muscle autophagy and atrophy, and to improve survival in mice with burn injury. Hosokawa, et al., *Efficacy of phosphodiesterase 5 inhibitor on distant burn-induced muscle autophagy, microcirculation, and survival rate, Am. J. Physiol. Endocrinol. Metab.* 304: E922-E933 (2013). However, PDE5 is not present in skeletal muscle tissue, but in the blood vessels in the muscles. Therefore, actions of PDE5 inhibitors, as the authors have suggested, may be due to improvements in burn-induced anomalies in blood flow and oxygen supply to skeletal muscles. It appears therefore that it will be advantageous to develop a combination therapy based on both PDE4B and PDE5 inhibitors because the direct therapeutic effects of PDE4B may be augmented by the beneficial effects of PDE5 inhibitors on blood flow.

PDE4B-Selective Inhibitors

Various PDE4B-selective inhibitors are known in the art. In 2014, Azam published a review of PDE4B-selective inhibitors and their structural design. Azam, et al., *Selective*

Phosphodiesterase 4B Inhibitors: A Review, Sci. Pharm. 82(3): 453-81 (2014), incorporated herein by reference in its entirety.

Recent studies have shown that PDE4B selectivity can be achieved by capturing a C-terminal regulatory helix domain, known as control region 3 (CR3), across the active site of PDE4B in a conformation that closes access by cAMP. Poondra, et al., Discovery of novel 1,4-dihydropyridine-based PDE4 inhibitors, Med. Chem. Lett. 23: 1104-09 (2013), incorporated herein by reference in its entirety.

Structural basis for design of PDE4B-selective inhibitors is further disclosed in Fox, et al., Structural basis for the design of selective phosphodiesterase 4B inhibitors, Cellular Signaling 26(3) 657-63 (2014), incorporated herein by reference in its entirety.

Specific selective PDE4B inhibitors are disclosed by Naganuma, et al., Discovery of selective PDE4B inhibitors, Bioorg. & Med. Chem. Lett. 19(12) 3174-76 (2009), incorporated herein by reference in its entirety.

In embodiments, suitable PDE4B-selective inhibitors are disclosed in U.S. Pat. Nos. 7,605,168 and 8,470,821, each of which is incorporated herein by reference in its entirety.

In certain embodiments, suitable PDE4B-selective inhibitors include, but are not limited to, the compounds set forth in Table 1, below. Table 1 compounds are disclosed in Naganuma at p. 3176.

TABLE 1

PDE4B Selective Inhibitors

| Compound Name | Structure |
| --- | --- |
| Compound 33 (4-{[2-(5-Chloro-2-thienyl)-5-ethyl-6-methyl-4-pyrimidinyl]amino}phenyl) acetic acid | (structure) |
| Compound 35 (4-{[5-Ethyl-2-(5-fluoro-2-thienyl)-6-methyl-4-pyrimidinyl]amino}-3-fluorophenyl)acetic acid | (structure) |

Methods

Accordingly, provided herein is a method of treating skeletal muscle cachexia associated with burn injury in a subject in need thereof, the method comprising administering to the subject an effective amount of a phosphodiesterase-4B (PDE4B)-selective inhibitor.

In certain embodiments, the PDE4B-selective inhibitor comprises a compound that acts by closing a control region 3 (CR3) C-terminal regulatory domain across an active site of PDE4B, thereby inhibiting PDE4B.

In certain embodiments, the PDE4B-selective inhibitor is selected from the group consisting of (4-{[2-(5-Chloro-2-thienyl)-5-ethyl-6-methyl-4-pyrimidinyl]amino}phenyl) acetic acid; (4-{[5-Ethyl-2-(5-fluoro-2-thienyl)-6-methyl-4-pyrimidinyl]amino}-3-fluorophenyl)acetic acid; and combinations thereof.

In some embodiments, the method further comprises administering to the subject an effective amount of a phosphodiesterase-5 (PDE5) inhibitor. In embodiments, the PDE4B-selective inhibitor and the PDE5 inhibitor are administered contemporaneously or sequentially.

In specific embodiments, the PDE5 inhibitor is selected from the group consisting of avanafil, lodenafil, mirodenafil, sildenafil, tadalafil, vardenafil, udenafil, zaprinast, benzamidenafil, and dasantafil.

In embodiments, the subject is a mammal. In a specific embodiment, the subject is selected from the group consisting of mouse, rat, rabbit, monkey, pig, and human. In a very specific embodiment, the subject is a human.

EXAMPLES

The following detailed methodology and materials are set forth to support and illustrate particular aspects and embodiments of the invention, and should not be construed as limiting the scope thereof.

Example 1. Materials and Methods

Animals

Well characterized PDE4B$^{+/-}$ breeding pairs with Sprague Dawley background (SD-Pde4b$^{tm1sage}$) were obtained from Horizon Discovery Group, St. Louis, Mo. (Cat No: TGRA7210), housed in a temperature controlled room (25° C.) under 12-h light/dark cycle, and maintained on standard rodent chow (Harlan Teklad Rodent Diet) and water ad libitum. These rats were generated using a pair of Zinc finger nucleases targeting exon1 of the rat PDE4B gene, and the 16 bp frameshift deletion (AGCGGCGTCGCTTCAC (SEQ ID NO: 1)) in exon 1 was verified by genomic DNA sequencing. Homozygous PDE4B$^{-/-}$ rats and the corresponding WT littermates (PDE4B$^{+/+}$) were obtained by mating heterozygous PDE4B$^{+/-}$ rats. The genetic makeup of the pups was identified by genotyping. The homozygous pairs thus obtained were used in subsequent breeding to continuously obtain the corresponding PDE4B$^{+/+}$ and PDE4B$^{-/-}$ rats, respectively. As has been previously reported for mice, PDE4B KO-rats appeared normal and exhibited litter size, body weight, and growth rate similar to those of WT littermates.

PCR

PCR studies were performed using proprietary primers for rat PDE4 isoforms obtained from Super Array Bioscience Corporation, Frederick, Md. The cAMP concentrations in muscle extracts were determined using an Elisa Kit (Cayman Chemicals, Ann Arbor, Mich.).

PDE and PDE4 Measurement

Skeletal muscle PDE and PDE4 activities were measured as described previously (Joshi, R., et al., Phosphodiesterase (PDE) inhibitor torbafylline (HWA 448) attenuates burn-induced rat skeletal muscle proteolysis through the PDE4/cAMP/EPAC/PI3K/Akt pathway, Mol. Cell. Endocrinol. 393: 152-63 (2014)).

Statistics

Figure 2:
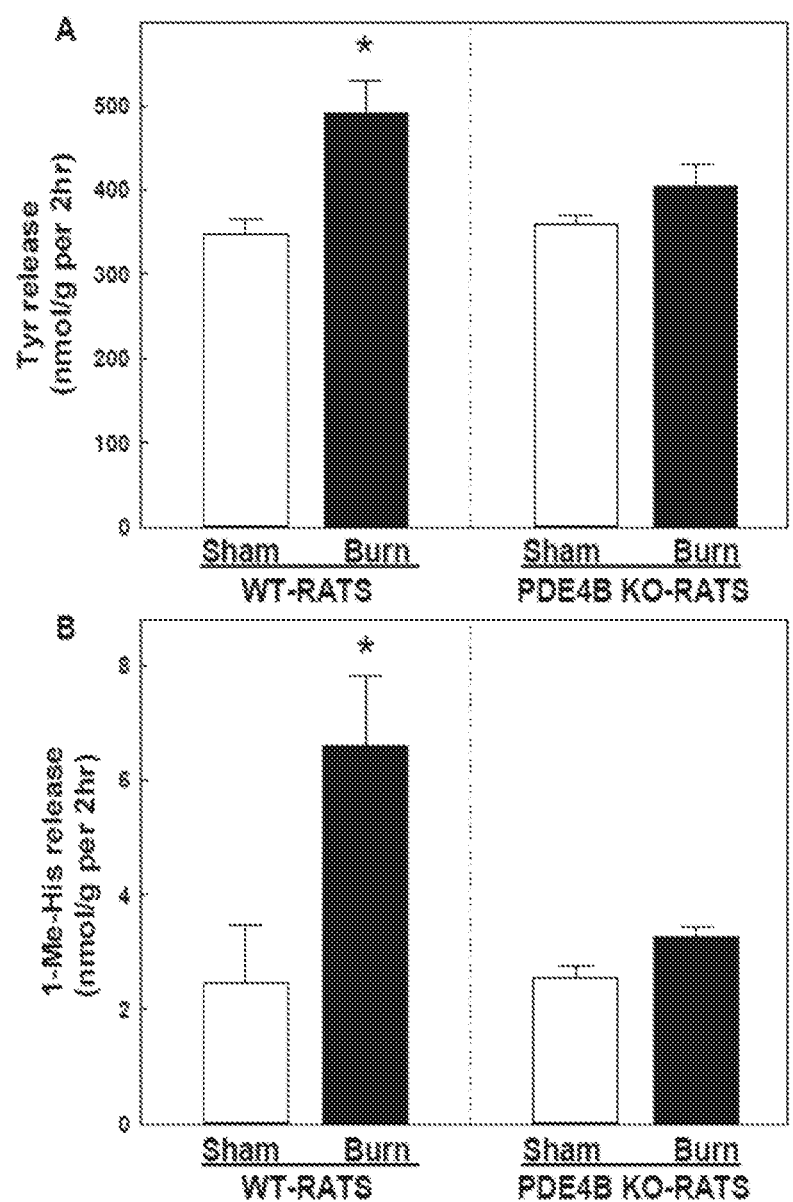
FIG. 2. Burn injury elevated EDL muscle protein breakdown 1 day after burn in WT rats, but had no effects in PDE4B KO rats. For both total (Tyr, A) and myofibrillar proteins (1-Me-His, B) breakdown was significantly elevated only in WT rats. * p<0.001 vs. all other groups, (n=8 (WT) and 13-15 (KO) per group).
Figure 3:
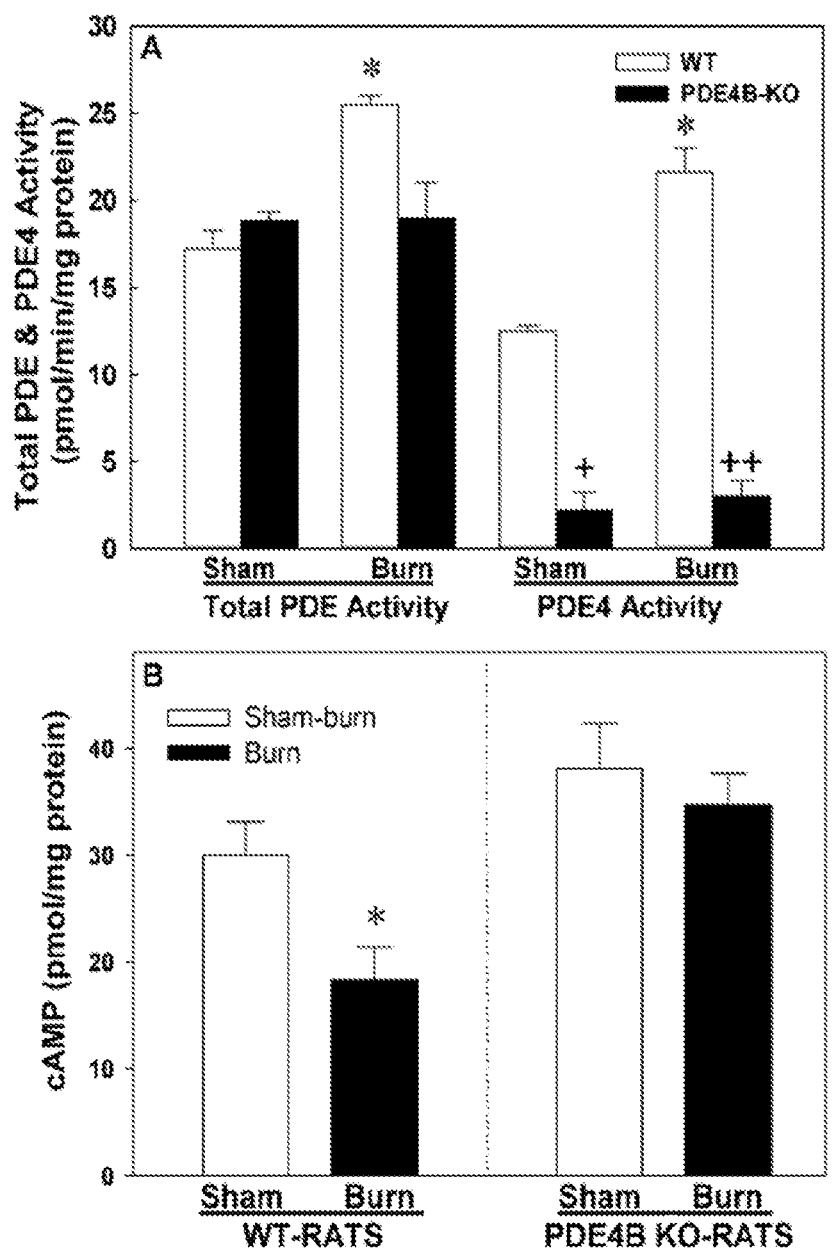
FIG. 3. Comparison of the effects of burn injury on skeletal muscle PDE and PDE4 activities, and cAMP concentrations in WT- and PDE4B KO-rats. (A) Effects of burn injury on total PDE and PDE4 specific activities in gastrocnemius muscle of WT- and PDE4B KO-rats 24 h after burn, (n=7-8 per group). * p<0.01 vs. all other groups; +p<0.001 vs. sham-WT; ++p<0.001 vs. burn-WT. (B) Effects of burn injury on cAMP concentration in the gastrocnemius muscle of WT- and PDE4B KO-rats 24 h after burn, (n=4-5 per group). * p<0.05 vs. sham-WT.
Figure 4:
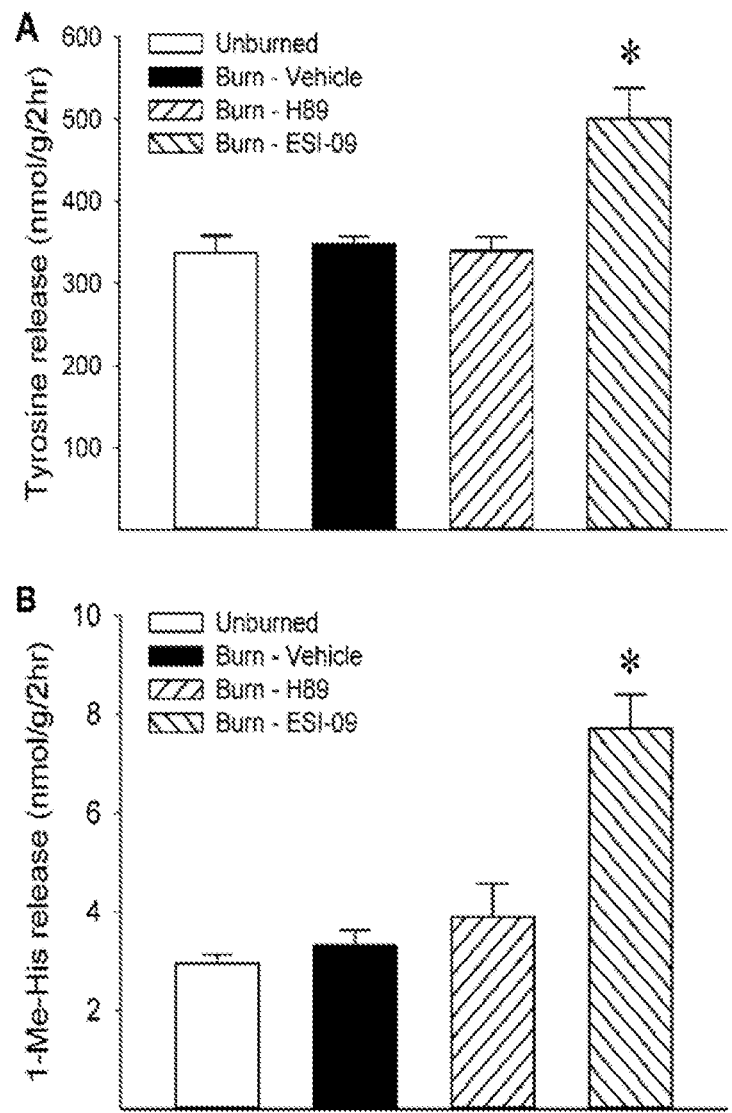
FIG. 4. Comparison of the effects of EPAC (ESI-09) and PKA (H89) inhibitors on PDE4B KO-induced resistance to skeletal muscle proteolysis in rats with burn injury. Effects of EPAC and and PKA inhibitors on total (A) and myofibrillar (B) protein breakdown during 2 h in vitro incubation of the EDL muscle of PDE4B KO rats obtained 24 h after burn, (n=6-8 per group). * p<0.05 vs. all other groups.

The mRNA data of each of the PDE4 primers were analyzed by Student's t-tests for differences between sham and burn rats (FIG. 1). The experimental design for the data involving both WT- and KO-rats was a two-way analysis of variance (ANOVA), with the two main effects of gene type (WT vs. KO) and treatment (burn vs. sham) (FIG. 2 and FIG. 3). Following overall statistical significance, pairwise comparisons by the Dunn-Sidak procedure were carried out. Comparison of the muscle protein breakdown in PDE4B KO-rats, KO burned-rats, and KO-rats+inhibitors of EPAC and PKA was done by a one-way ANOVA and followed by the Dunn-Sidak test for multiple comparisons (FIG. 4). Data on figures are expressed as mean±SEM. SAS, version 9.4 (SAS Institute, Cary, N.C.) was used to analyze data and statistical significance was set at P<0.05. Real time PCR data, Ct value analysis, standard curves and relative quantity of fluorescence were calculated using a software program in the MX-3000P instrument. A P value of <0.05 was considered statistically significant.

Example 2. Effect of PDE4B Knockout on Protein Breakdown after Burn Injury

Young homozygous PDE4B KO- and WT-rats (65-75 g) were used in the muscle incubation studies because they possess lower extremity muscles thin enough to permit diffusion of oxygen from the medium, thus preventing the development of hypoxic regions in the muscles. Sixteen each of WT- and PDE4B KO-male rats were anesthetized with pentobarbital (50 mg/kg), and their backs were shaved. Of these 32 rats, eight each of WT- and PDE4B KO-rats were then subjected to a 16 s third-degree open flame burn on the back, affecting 30% of total body surface area (TBSA). Both burned and unburned rats were then resuscitated with 0.9% NaCl (10 ml/100 g body weight, intraperitoneally). The unburned rats constituted the respective sham groups. All rats were provided with rat chow equivalent to ~10% of their body weight, based on previous observations that burned rats consumed food≤10% of their body weight within the first 24 h after burn injury.

After 24 h, rats were re-anesthetized with pentobarbital (50 mg/kg), and the gastrocnemius muscles were dissected and rapidly frozen in liquid nitrogen. To assess protein breakdown rates, the dissected extensor digitorum longus (EDL) muscles were tied by the tendons at resting length to stainless steel supports and preincubated in a shaking water bath for 30 min at 37° C. in individually stoppered 25 ml flasks containing 3 ml oxygenated (95% $O_2$-5% $CO_2$) Krebs-Henseleit bicarbonate buffer (pH 7.4) with 10 mM glucose. Muscles were then transferred to fresh buffer containing 0.5 mM cycloheximide for 2 h incubation. The total (tyrosine) and myofibrillar (1-methyl-histidine, 1-Me-His) protein breakdown rates were determined by measuring the net production of tyrosine and 1-Me-His during 2 h incubation, according to previously published HPLC procedures (Balasubramaniam, A., et al., *Torbafylline (HWA 448) inhibits skeletal muscle proteolysis in burned rats, J. Burn Care & Res.* 30: S151 (2009)). The protein breakdown studies with PDE4B KO-rats were repeated with eight each of sham and burn rats to corroborate our initial findings. Additional in vivo experiments were performed to obtain tissues for biochemical studies and to study the effects of inhibitors of PKA (H89) and EPAC (ESI-09) on EDL protein breakdown in PDE4B KO-rats.

Burn injury significantly (p<0.001) increased Tyr (348±17→490±38 nmol/g/2h, 41% increase) and 1-Me-His (2.46±0.99→6.56±1.23, 167%) release from the EDL muscle of WT-rats compared to that of WT-sham controls (FIGS. 2A and 2B). Moreover, a comparison of the genotype effects revealed that burn injury exhibited significantly (p<0.001) greater effects in promoting EDL muscle protein breakdown (Tyr: 41% vs. 11%; 1-Me-His: 167% vs. 28%) in WT-rats than that by the EDL of burn-PDE4B KO-rats. Burn injury also increased release of Tyr (324±10→360±15, 11%) and 1-Me-His (2.54±0.22→3.26±0.17, 28%) from the EDL muscle of PDE4B KO-rats compared to that of sham-PDE4B KO controls (FIGS. 2A and 2B), but these changes were not statistically significant.

Burn injury increased gastrocnemius muscle total PDE and PDE4 activities by ~50% and ~70%, respectively, in WT-rats (FIG. 3A). However, PDE4B KO prevented any burn-associated increase in total PDE activity in the gastrocnemius muscle and substantially decreased the PDE4 activity by >80% in the gastrocnemius muscle of both sham- and burn-rats. Burn injury significantly decreased the gastrocnemius muscle cAMP concentration by ~40% compared to that of the sham controls, but had no significant effects on the gastrocnemius muscles cAMP concentration of PDE4B-KO rats (FIG. 3B).

Example 3. Effect of Inhibitors of cAMP Downstream Elements on Protein Breakdown after Burn Injury To elucidate the factor(s) imparting resistance to burn-induced skeletal muscle proteolysis in PDE4B-KO rats, EDL muscles of burn-PDE4B KO rats were incubated in the presence of inhibitors for cAMP downstream elements, PKA (H89) and EPAC (ESI-09). These studies indicated that ESI-09 alleviated PDE4B KO-induced resistance and promoted burn-induced EDL muscle total and myofibrillar protein breakdown to the same extent as in the EDL muscle of burn-WT rats (FIGS. 4A and 4B). H89 did not exhibit any effect.

Example 4. Effect of Burn Injury on mRNA Expression of PDE4 Isoforms in EDL 16 male Sprague Dawley rats (60-75 g) from Harlan laboratories, IN, were obtained and subjected to sham-burn (n=8) and burn (n=8) procedures as described above to investigate the effects of burn injury on the mRNA expression of PDE4 isoforms in the EDL.

Modulations in mRNA expression of PDE4 isoforms were investigated in the EDL muscles 24h after burn injury. Burn injury increased the mRNA expression of PDE4B by 6-fold (FIG. 1). On the other hand, burn injury significantly (p<0.001) decreased the mRNA expression of PDE4A compared to its sham controls. There were no significant changes in the expression of PDE4C and PDE4D.

Figure 5:
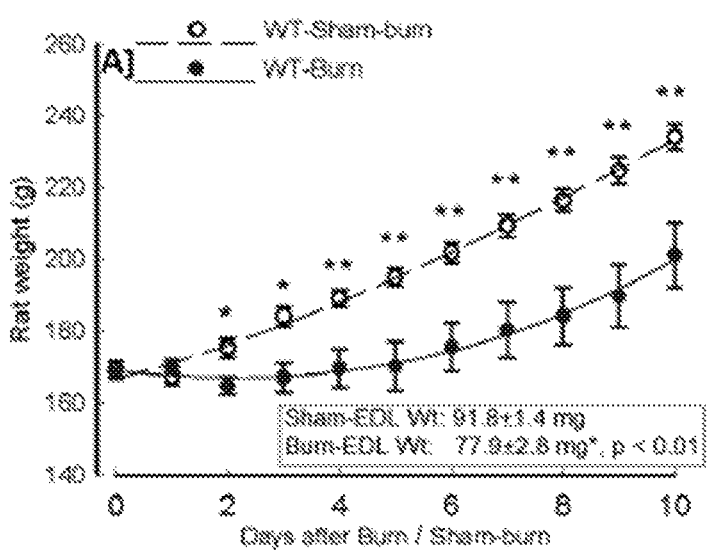
FIG. 5. Thirty percent total body surface area (TBSA) burn of adult rats significantly (** p<0.01 vs sham-rats) retarded body weight gain in WT rats compared to that of sham-WT rats over 10 days after burn injury (A), but had no effects in burn-PDE4B KO-rats, which gained body weight to the same extent as the sham-PDE4B KO-rats (B). Similarly, burn injury significantly (p<0.01 vs. controls) reduced the EDL muscle weight of WT-rats over 10-days compared to that of sham-WT rats (A-box insert), but had no significant effects in that of burn-PDE4B KO-rats (B-box insert).
Figure 5:
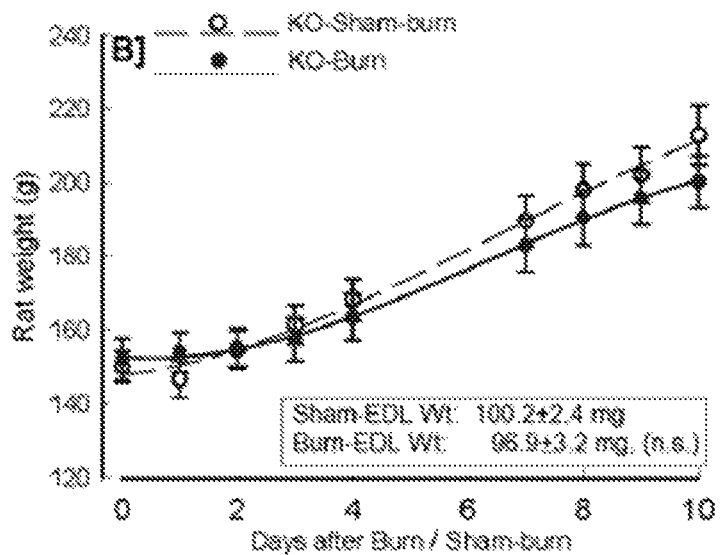

Example 5. PDE4B Knockout Restores Body Weight Gain in Adult Burn Rats Over 10 Days As shown in FIG. 5, burn injury caused a significant retardation in body weight gain over 10 days in adult WT rats, but burn-PDE4B KO rats gained body weight to the same extent as the sham-PDE4B KO-rats (FIGS. 5A and 5B). In agreement, EDL muscle weight was significantly reduced in WT rats 10-days after burn injury, but EDL muscle weight of burn-PDE4B KO rats remained comparable to that of sham-PDE4B KO rats after 10-days (See box inserts in FIGS. 5A and 5B). These observations suggest that PDE4B may be primarily be responsible for: 1) skeletal muscle proteolysis in adult burn-rats; and 2) long-term muscle dysfunctions in burn injury.

Example 6. Pre-Treatment with a PDE4B-Selective Inhibitor Ameliorates Skeletal Muscle Cachexia Adult WT rats are pre-treated with either PDE4B-selective inhibitor (4-{[2-(5-Chloro-2-thienyl)-5-ethyl-6-methyl-4-pyrimidinyl]amino}phenyl)acetic acid (test group) or saline (control group). Rats are treated daily for 7 days prior to burn exposure. On day 8, rats are anaesthetized, shaved, and subjected to a third-degree burn on the back, affecting 30% of total body surface area (TBSA). Both test WT rats and control WT rats are then resuscitated. All rats are provided with rat chow equivalent to ~10% of their body weight.

After 24 h, all rats are re-anesthetized and the gastrocnemius muscles are dissected and rapidly frozen in liquid nitrogen. To assess protein breakdown rates, the dissected extensor digitorum longus (EDL) muscles are tied by the tendons at resting length to stainless steel supports and preincubated in a shaking water bath for 30 min at 37° C. in individually stoppered 25 ml flasks containing oxygenated (95% $O_2$-5% $CO_2$) Krebs-Henseleit bicarbonate buffer (pH 7.4) with 10 mM glucose. Muscles are then transferred to fresh buffer containing 0.5 mM cycloheximide for 2 h incubation. The total (tyrosine) and myofibrillar (1-methyl-histidine, 1-Me-His) protein breakdown rates are determined by measuring the net production of tyrosine and 1-Me-His during 2 h incubation.

Pre-treatment of WT rats with PDE4B-selective inhibitor significantly decreases Tyr and 1-Me-His release from the EDL muscle compared to that of control WT rats.

All documents cited are incorporated herein by reference; the citation of any document is not to be construed as an admission that it is prior art with respect to the present invention.

It is to be further understood that where descriptions of various embodiments use the term "comprising," and/or "including" those skilled in the art would understand that in some specific instances, an embodiment can be alternatively described using language "consisting essentially of" or "consisting of."

While particular embodiments of the present invention have been illustrated and described, it would be obvious to one skilled in the art that various other changes and modifications can be made without departing from the spirit and scope of the invention. It is therefore intended to cover in the appended claims all such changes and modifications that are within the scope of this invention.

---

---

We claim:

1. A method of treating skeletal muscle cachexia associated with burn injury in a subject in need thereof, the method comprising administering to the subject an effective amount of a phosphodiesterase-4B (PDE4B)-selective inhibitor selected from the group consisting of (4-{[2-(5-Chloro-2-thienyl)-5-ethyl-6-methyl-4-pyrimidinyl]amino}phenyl) acetic acid, (4-{[5-Ethyl-2-(5-fluoro-2-thienyl)-6-methyl-4-pyrimidinyl]amino}-3-fluorophenyl)acetic acid, and combinations thereof.

2. The method according to claim 1, wherein the PDE4B-selective inhibitor comprises a compound that acts by closing a control region 3 (CR3)C-terminal regulatory domain across an active site of PDE4B, thereby inhibiting PDE4B.

3. The method according to claim 1, further comprising administering to the subject an effective amount of a phosphodiesterase-5 (PDE5) inhibitor selected from the group consisting of avanafil, lodenafil, mirodenafil, sildenafil, tadalafil, vardenafil, udenafil, zaprinast, benzamidenafil, and dasantafil.

4. The method according to claim 3, wherein the PDE4B-selective inhibitor and the PDE5 inhibitor are administered contemporaneously or sequentially.

5. The method according to claim 1, wherein the subject is a mammal.

6. The method according to claim 5, wherein the subject is selected from the group consisting of mouse, rat, rabbit, monkey, pig, and human.

7. The method according to claim 6, wherein the subject is a human.

\* \* \* \* \*

SEQUENCE LISTING

```
<160> NUMBER OF SEQ ID NOS: 1

<210> SEQ ID NO 1
<211> LENGTH: 16
<212> TYPE: DNA
<213> ORGANISM: Rattus rattus
<220> FEATURE:
<221> NAME/KEY: misc_feature
<223> OTHER INFORMATION: 16 bp frameshift deletion in exon 1 of rat
      PDE4B gene

<400> SEQUENCE: 1
agcggcgtcg cttcac                                                 16
```